(12) United States Patent
Liu et al.

(10) Patent No.: US 6,388,576 B1
(45) Date of Patent: May 14, 2002

(54) MINITYPE ALCOHOL EXCESSIVE WARNING DEVICE

(76) Inventors: Ko-Chien Liu, 29, Nong 11, Lane 76, Zhong-Cheng Rd., Hsin-Dien City, Taipei Hsien; Yi-Chia Shen, Floor 8, No. 54, Sec. 2, HanKo St., Taipei City; Ching-Piao Lin, 14-2, Nong 7, Lane 200, Min-Chuan Rd., Ban-Chiao City, Taipei Hsien; Yao-Tsung Chang, Floor 8, No. 251, An-Le Rd., Chung-Ho City, Taipei Hsien, all of (TW)

( * ) Notice: Subject to any disclaimer, the term of this patent is extended or adjusted under 35 U.S.C. 154(b) by 0 days.

(21) Appl. No.: 09/822,049

(22) Filed: Mar. 30, 2001

(51) Int. Cl.⁷ .............................................. G08B 23/00
(52) U.S. Cl. ....................... 340/576; 340/321; 340/573; 73/23
(58) Field of Search ................................ 340/576, 439, 340/321, 573; 128/719; 73/23; 422/84

(56) References Cited

U.S. PATENT DOCUMENTS

| 3,877,291 A | * | 4/1975 | Hoppesch et al. | ........... 73/23.3 |
| 4,093,945 A | * | 6/1978 | Collier et al. | ................ 340/279 |
| 4,274,425 A | * | 6/1981 | Lutz et al. | ................... 128/719 |
| 4,300,384 A | * | 11/1981 | Wiesner et al. | ................. 73/23 |
| 4,314,564 A | * | 2/1982 | Albarda | ....................... 128/719 |
| 4,487,055 A | * | 12/1984 | Wolff | ............................. 73/23 |
| 4,749,553 A | * | 6/1988 | Lopez et al. | ................... 422/84 |
| 4,868,545 A | * | 9/1989 | Jones | .......................... 340/573 |
| 4,996,161 A | * | 2/1991 | Conners et al. | ............. 436/132 |

\* cited by examiner

Primary Examiner—Daniel J. Wu
Assistant Examiner—Phung Nguyen
(74) Attorney, Agent, or Firm—Charles E. Baxley

(57) ABSTRACT

A minitype alcohol excessive warning device includes a detecting circuit consisting of a power circuit, a delay circuit, and a sensing circuit. The detecting circuit is mounted in a housing having a simple structure, thereby constructing a miniature alcohol excessive warning device. In such a manner, the minitype alcohol excessive warning device has a low cost, can be used easily and conveniently, and is portable.

8 Claims, 4 Drawing Sheets

MINITYPE ALCOHOL EXCESSIVE WARNING DEVICE

BACKGROUND OF THE INVENTION

1. Field of the Invention

The present invention relates to a minitype alcohol excessive warning device.

2. Description of the Related Prior Art

A conventional alcoholic concentration detecting device includes precise components to detect the alcoholic concentration accurately. However, the conventional alcoholic concentration detecting device has a large volume with an expensive cost, so that it is unavailable to the ordinary people, thereby greatly limiting the utility of the conventional alcoholic concentration detecting device.

SUMMARY OF THE INVENTION

The primary objective of the present invention is to provide a minitype alcohol excessive warning device which has a low cost, can be used easily and conveniently, and is portable.

In accordance with the present invention, there is provided a minitype alcohol excessive warning device comprising a housing, and a detecting circuit;

wherein, the housing contains a receiving space therein, and has an outer periphery formed with a plurality of detecting openings communicating with the receiving space, the detecting circuit is mounted in the receiving space of the housing, and includes a sensor mating with the detecting openings, the detecting circuit further includes a power supply indicating lamp, a stand-by indicating lamp, and an excess warning lamp each emitting light outward from the housing.

The detecting circuit includes a power circuit, a delay circuit, and a sensing circuit, wherein:

the power circuit includes a battery co-operating with a power switch for supplying power, and a voltage decrease resistor serially connected with the power supply indicating lamp for indicating a power connection;

the delay circuit includes a first comparator, a delay resistor, a delay capacitor, a first signal detecting resistor, and the stand-by indicating lamp, the first comparator includes a negative input side that can obtain an input signal through the first signal detecting resistor, a positive input side connected to the delay resistor and the delay capacitor, and an output side connected to the stand-by indicating lamp, such that after the detecting circuit has been energized by the battery, the stand-by indicating lamp can be delayed to light during a predetermined period of time;

the sensing circuit includes a second comparator, a second signal detecting resistor, the sensor, an adjustable resistor, a mating resistor, and the excess warning lamp, wherein the second comparator includes a positive input side that can obtain an input signal through the second signal detecting resistor, a negative input side connected to the sensor and the adjustable resistor to obtain a detecting signal, and an output side connected to the excess warning lamp, the sensor has a first end connected to a power supply and a second end connected to the mating resistor to obtain an electric power, and the adjustable resistor is variable to preset an operation basis value of the second comparator.

Further benefits; and advantages of the present invention will become apparent after a careful reading of the detailed description with appropriate reference to the accompanying drawings.

DETAILED DESCRIPTION OF THE INVENTION

Figure 1:
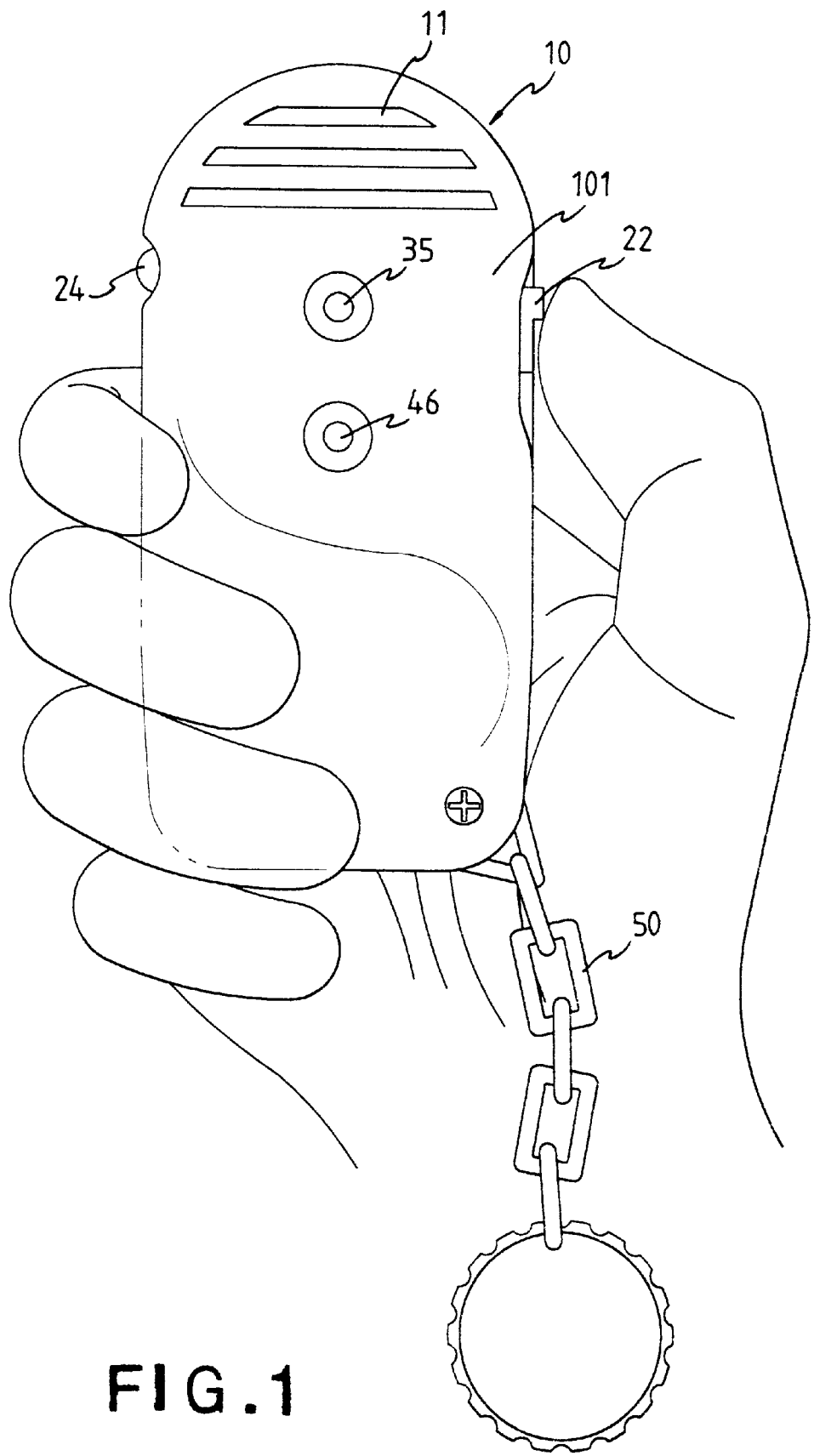
FIG. 1 is a front plan schematic view of a minitype alcohol excessive warning device in accordance with the present invention.
Figure 2:
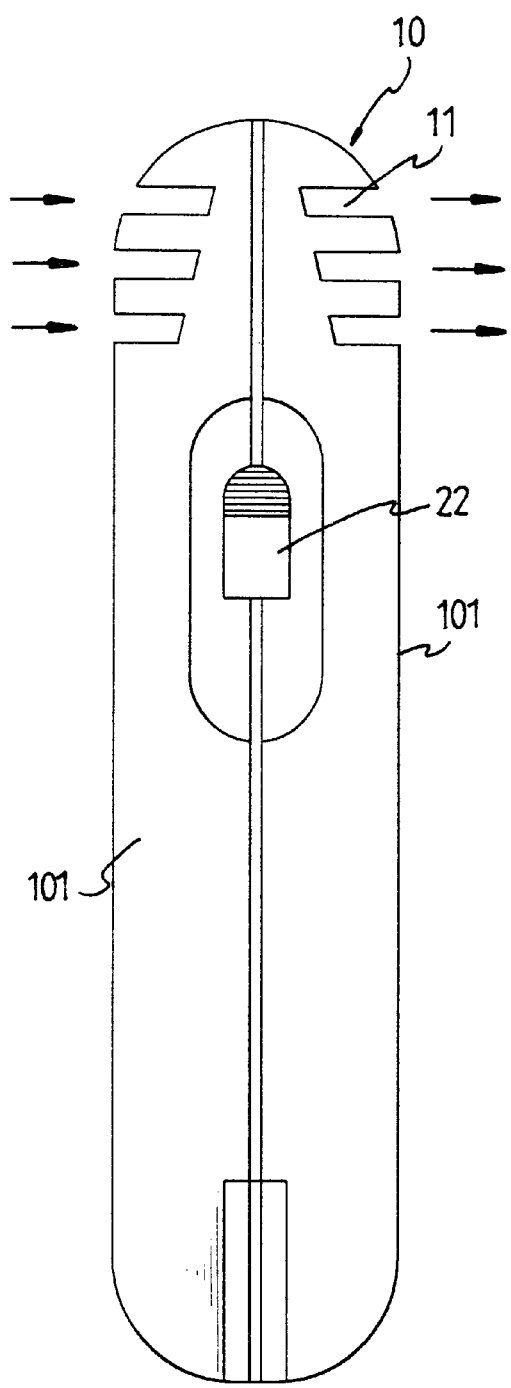
FIG. 2 is a side plan view of the minitype alcohol excessive warning device as shown in FIG. 1.
Figure 3:
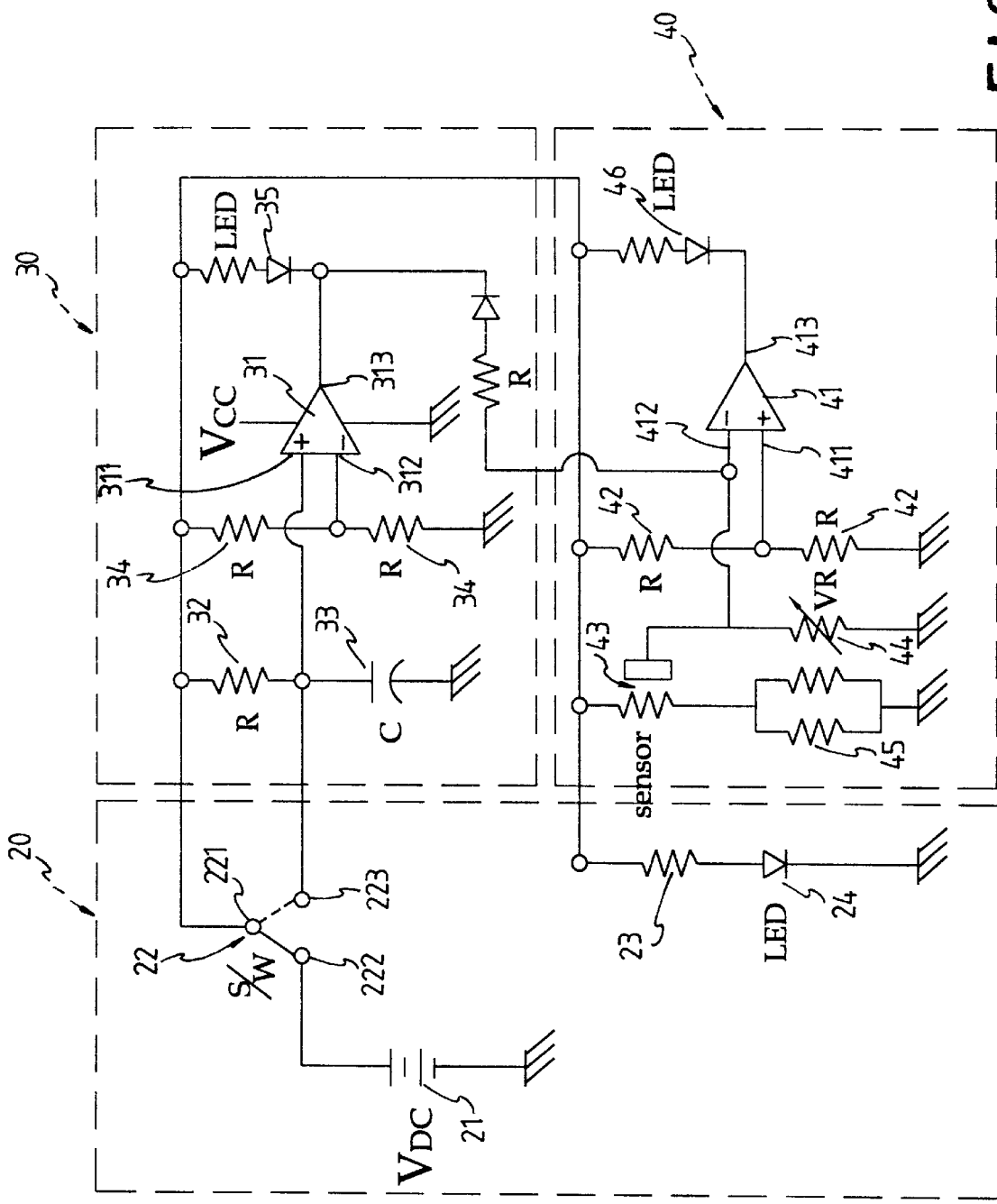
FIG. 3 is a circuit diagram of the minitype alcohol excessive warning device as shown in FIG. 1.

Referring to the drawings and initially to FIGS. 1–3, a minitype alcohol excessive warning device in accordance with the present invention comprises a housing 10, and a detecting circuit.

The housing 10 is constructed by two shells 101, thereby forming a receiving space therein. The housing 10 has an outer periphery formed with a plurality of detecting openings 11 communicating with the receiving space. Each detecting opening 11 is extended through the two sides of the housing 10 as shown in FIG. 2. Preferably, the housing 10 is a light permeable housing.

As shown in FIG. 3, the detecting circuit includes a power circuit 20, a delay circuit 30, and a sensing circuit 40.

The power circuit 20 includes a battery 21 co-operating with a power switch 22 for supplying the electric power to the detecting circuit. The power switch 22 includes a control connection point 221, a close connection point 222, and an open connection point 223. When the control connection point 221 is connected with the close connection point 222, the detecting circuit is connected with and energized by the power supply of the battery 21. When the control connection point 221 is connected with the open connection point 223, the detecting circuit is disconnected with the power supply of the battery 21. A voltage decrease resistor 23 is mounted on a line connected to the control connection point 221, and is serially connected with a power supply indicating lamp 24 for indicating that the power supply is disposed at connection state. The power supply indicating lamp 24 may be formed by a green LED, and may emit the light outward from the housing 10.

The delay circuit 30 includes a comparator 31, a delay resistor 32, a delay capacitor 33, a signal detecting resistor 34, and a stand-by indicating lamp 35. The stand-by indicating lamp 35 may be formed by a yellow LED. The comparator 31 includes a negative input side 312 that can obtain an input signal (obtain the basis,, signal from the power supply) through the signal detecting resistor 34, a positive input side 311 connected to the delay resistor 32 and the delay capacitor 33, and an output side 313 connected to the stand-by indicating lamp 35. The delay resistor 32 and the delay capacitor 33 of the delay circuit 30 have a lime constant RC representing a delay time which may be equal to ten seconds (in the preferred embodiment) by changing the value of the delay resistor 32 and the value of the delay capacitor 33. Thus, after the detecting circuit has been energized by the battery 21, the stand-by indicating lamp 35 can be delayed to emit light during a predetermined period of time, e.g., ten seconds (in practice, the pre-heating time required for the sensor is from five to eight seconds). The stand-by indicating lamp 35 may emit light outward from the housing 10.

The sensing circuit 40 includes a comparator 41, a signal detecting resistor 42, a sensor 43, an adjustable resistor 44, a mating resistor 45, and an excess warning lamp 46. The excess warning lamp 46 may be formed by a red LED. The comparator 41 includes a positive input side 411 that can obtain an input signal through the signal detecting resistor 42 (obtain the basis signal from the power supply), a negative input side 412 connected to the sensor 43 and the adjustable resistor 44 to obtain a detecting signal, and an output side 413 connected to the excess warning lamp 46. The sensor 43 has a first end connected to the power supply and a second end connected to the mating resistor 45 to obtain the electric power. The excess warning lamp 46 may emit light outward from the housing 10. The sensor 43 is mounted in the housing 10 to mate with the detecting openings 11. The adjustable resistor 44 is variable to preset the operation basis value of the comparator 41. The sensing circuit 40 has an alcohol concentration detection basis value which may be preset by changing the value of the adjustable resistor 44. In the preferred embodiment, the alcohol concentration detection basis value may be preset to be equal to 0.25 mg/l.

In the present invention, the sensor 43 can be used to detect the tiny particles in the gas. Sensors of different features can be used to detect different kinds of gases, such as sulphide, carbon monoxide, carbon dioxide, carbide or the like. The sensor 43 can convert the detecting results into the resistance values. In use, the sensor 43 has to be preheated during a predetermined period of time before detection. In the preferred embodiment, the pre-heated time required for the sensor 43 is from five to eight seconds. When air containing alcoholic tiny particles passes through the sensor 43, the resistance value of the sensor 43 is decreased. In practice, the concentration of the alcoholic tiny particles is inversely proportional to the resistance value of the sensor 43. Thus, if the alcoholic concentration is increased, the resistance value of the sensor 43 is decreased.

Figure 4:
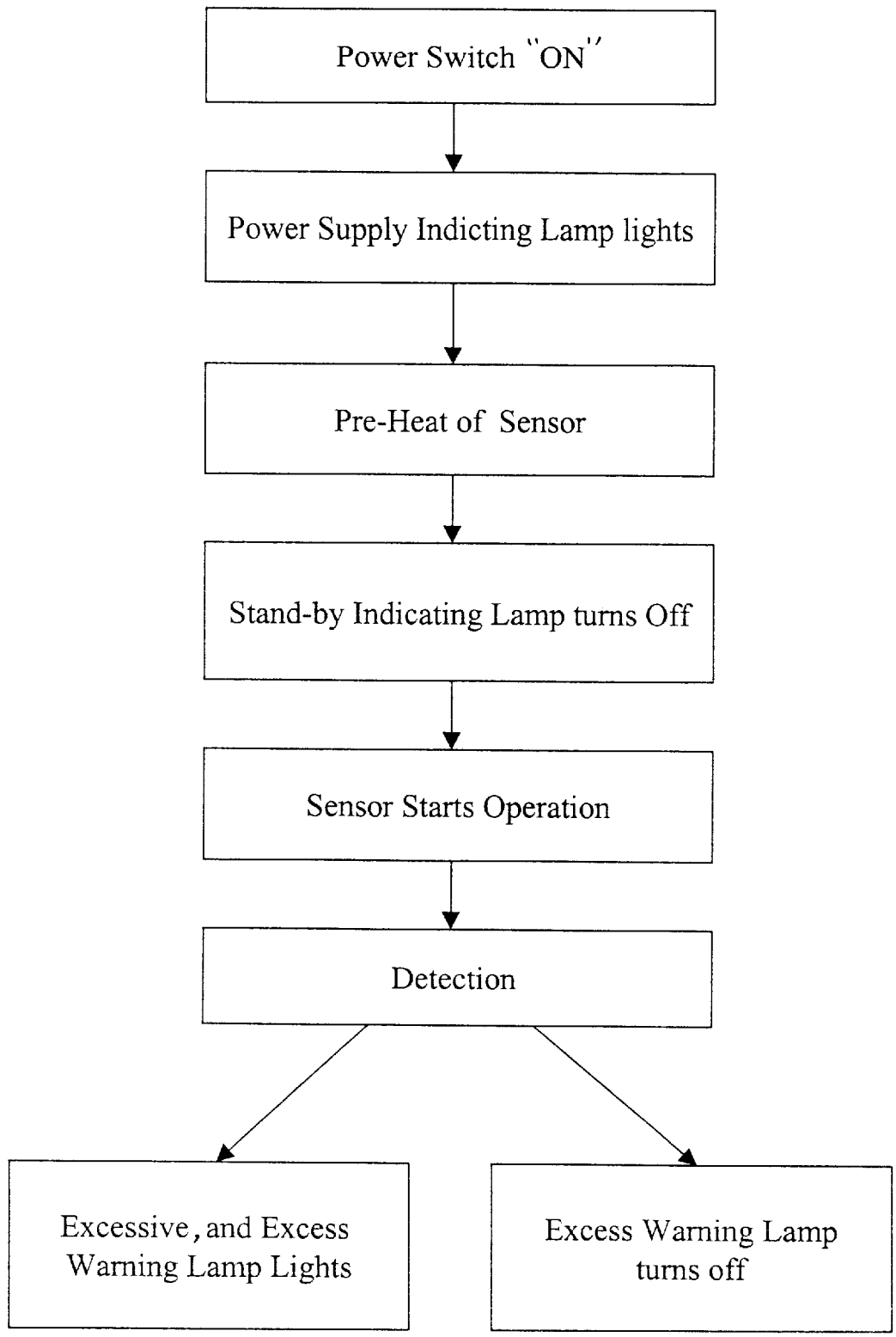
FIG. 4 is a flow chart of the minitype alcohol excessive warning device as shown in FIG. 1.

Referring to FIG. 4, the power switch 22 is switched to the "ON" position, whereby the control connection point 221 is connected with the close connection point 222, so that the detecting circuit may be connected with and energized by the power supply of the battery 21. At the same time, the green light of the power supply indicating lamp 24 lights. The delay resistor 32 of the delay circuit 30 co-operates with the delay capacitor 33 to proceed the charging and discharging action simultaneously, and then to transmit the signal to the comparator 31 to be output, so that the yellow light of the stand-by indicating lamp 35 may light during ten seconds by changing the value of the delay resistor 32 and the value of the delay capacitor 33. At the same time, the sensor 43 is energized and heated during five to eight seconds, until the stand-by indicating lamp 35 turns off (after ten seconds). Thus, pre-heated process of the sensor 43 is complete, and the sensor 43 is ready for detection.

In use, the user may blow air toward the detecting openings 11 of the housing 10. The resistance value of the sensor 43 will change if the airflow contains the alcoholic tiny particles. In the preferred embodiment, the alcohol concentration detection basis value may be preset to 0.25 mg/l by changing the value of the adjustable resistor. When the alcohol concentration contained in the airflow exceeds the basis value, the resistance value of the sensor 43 is very low, so that the comparator 41 of the sensing circuit 40 is operated, so as to drive the red light of the excess warning lamp 46 to light. When the alcohol concentration contained in the airflow is lower than the basis value, the resistance value of the sensor 43 is very high, so that the excess warning lamp 46 is not operated. The power switch 22 may be switched to the "OFF" position after the detection process, whereby the control connection point 221 is disconnected with the close connection point 222, so that the detecting circuit stops operation.

Accordingly, the circuit volume of the present invention may be designed to have a very small status, thereby facilitating the user carrying the minitype alcohol excessive warning device. As shown in FIG. 1, the minitype alcohol excessive warning device may be attached to a key ring 50. In addition, the cost is very low. When the power switch 22 is opened, the power supply indicating lamp 24 normally lights for providing an illuminant effect. It is appreciated that the lighting time of the excess warning lamp 46 is proportional to the amount of the airflow blown by the user. The excess warning lamp 46 will light if the alcohol concentration contained in the airflow exceeds the basis value of 0.25 mg/l. The lighting time of the excess warning lamp 46 is short if the amount of the airflow blown by the user is little, and the lighting time of the excess warning lamp 46 is longer if the amount of the airflow blown by the user is more, thereby preventing the person to be detected from blowing little amount of airflow.

While the preferred embodiment of the present invention has been shown and described, it will be apparent to those skilled in the art that various modifications may be made in the embodiment without departing from the spirit of the present invention. Such modifications are all within the scope of the present invention.

What is claimed is:

1. A minitype alcohol excessive warning device comprising a housing (10), and a detecting circuit;

wherein, said housing (10) contains a receiving space therein, and has an outer periphery formed with a plurality of detecting openings (11) communicating with said receiving space, said detecting circuit is mounted in said receiving space of said housing (10), and includes a sensor (43) mating with said detecting openings (11), said detecting circuit further includes a power supply indicating lamp (24), a stand-by indicating lamp (35), and an excess warning lamp (46) each emitting light outward from said housing (10); and said detecting circuit further includes a power circuit (20), a delay circuit (30), and a sensing circuit (40), wherein:

said power circuit (20) includes a battery (21) co-operating with a power switch (22) for supplying power, and a voltage decrease resistor (23) serially connected with said power supply indicating lamp (24) for indicating a power connection;

said delay circuit (30) includes a first comparator (31), a delay resistor (32), a delay capacitor (33), a first signal detecting resistor (34), and said stand-by indicating lamp (35), said first comparator (31) includes a negative input side (312) that can obtain an input signal through said first signal detecting resistor (34), a positive input side (311) connected to said delay resistor (32) and said delay capacitor (33), and an output side (313) connected to said stand-by indicating lamp (35), such that after said detecting circuit has been energized by said battery (21), said stand-by indicating lamp (35) can be delayed to light during a predetermined period of time; and said sensing circuit (40) includes a second comparator (41), a second signal detecting resistor (42), said sensor (43), an adjustable resistor (44), a mating resistor (45), and said excess warning lamp (46), wherein said second comparator (41) includes a positive input side (411) that can obtain an input signal through said second signal detecting resistor (42), a negative input side (412) connected to said sensor (43) and said adjustable resistor (44) to obtain a detecting signal, and an output side (413) connected to said excess warning lamp (46), said sensor (43) has a first end connected to a power supply and a second end connected to said mating resistor (45) to obtain an electric power, and said adjustable resistor (44) is variable to preset an operation basis value of said second comparator (41).

2. The minitype alcohol excessive warning device in accordance with claim 1, wherein said housing (10) is light permeable.

3. The minitype alcohol excessive warning device in accordance with claim 1, wherein said power switch (22) includes a control connection point (221), a close connection point (222), and an open connection point (223), so that when said control connection point (221) is connected with said close connection point (222), said detecting circuit is connected with and energized by said power supply, and when said control connection point (221) is connected with said open connection point (223), said detecting circuit is disconnected with said power supply.

4. The minitype alcohol excessive warning device in accordance with claim 1, wherein said power supply indicating lamp (24) is formed by green LED.

5. The minitype alcohol excessive warning device in accordance with claim 1, wherein said stand-by indicating lamp (35) is formed by a yellow LED.

6. The minitype alcohol excessive warning device in accordance with claim 1, wherein said excess warning lamp (46) is formed by a red LED.

7. The minitype alcohol excessive warning device in accordance with claim 1, wherein said delay resistor (32) and said delay capacitor (33) of said delay circuit (30) have a time constant RC representing a delay time which may be equal to ten seconds by changing a value of said delay resistor (32) and a value of said delay capacitor (33).

8. The minitype alcohol excessive warning device in accordance with claim 1, wherein said sensing circuit (40) has an alcohol concentration detection basis value which may be equal to 0.25 mg/l by changing a value of said adjustable resistor (44).

* * * * *